United States Patent
Rabhi et al.

(10) Patent No.: US 10,596,216 B2
(45) Date of Patent: *Mar. 24, 2020

(54) **USE OF A *WITHANIA* EXTRACT FOR THE TREATMENT OF AMYLOID-RELATED DISEASES**

(71) Applicants: Ethnodyne, Paris (FR); Centre National de la Recherche Scientifique (CNRS), Paris (FR)

(72) Inventors: Chérif Rabhi, Bretigny sur Orge (FR); Léon Cariel, Paris (FR); Jamal Ouazzani, Massy (FR); Guillaume Arcile, Les Ulis (FR)

(73) Assignee: Ethnodyne and Centre National de la Recherche Scientifique (CNRS), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/560,975

(22) PCT Filed: Mar. 23, 2015

(86) PCT No.: PCT/EP2015/056132
§ 371 (c)(1),
(2) Date: Sep. 22, 2017

(87) PCT Pub. No.: WO2016/150481
PCT Pub. Date: Sep. 29, 2016

(65) Prior Publication Data
US 2018/0042979 A1  Feb. 15, 2018

(51) Int. Cl.
| | |
|---|---|
| *A61K 36/00* | (2006.01) |
| *A61K 36/81* | (2006.01) |
| *A61K 36/9066* | (2006.01) |
| *A61K 36/185* | (2006.01) |
| *A61K 36/28* | (2006.01) |
| *A61K 36/67* | (2006.01) |
| *A61K 36/47* | (2006.01) |
| *A61K 36/80* | (2006.01) |
| *A61K 36/068* | (2006.01) |
| *A61K 9/00* | (2006.01) |
| *A61K 36/68* | (2006.01) |

(52) U.S. Cl.
CPC ............ *A61K 36/81* (2013.01); *A61K 9/0019* (2013.01); *A61K 9/0053* (2013.01); *A61K 36/068* (2013.01); *A61K 36/185* (2013.01); *A61K 36/28* (2013.01); *A61K 36/47* (2013.01); *A61K 36/67* (2013.01); *A61K 36/68* (2013.01); *A61K 36/80* (2013.01); *A61K 36/9066* (2013.01); *A61K 2236/19* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 2006/0147554 A1* | 7/2006 | Palpu | A23F 3/34 424/725 |
| 2010/0021533 A1 | 1/2010 | Mazed et al. | |
| 2011/0274680 A1 | 11/2011 | Mazed et al. | |

FOREIGN PATENT DOCUMENTS

| | | |
|---|---|---|
| CN | 102329837 A * | 1/2012 |
| WO | 2010/013254 A2 | 2/2010 |
| WO | 2014/202469 A1 | 12/2014 |

OTHER PUBLICATIONS

International Search Report dated Jun. 23, 2015, issued in corresponding International Application No. PCT/EP2015/056132, filed Jun. 12, 2015, 3 pages.
Mathew, M., and S. Subramanian, "In Vitro Screening for Anti-Cholinesterase and Antioxidant Activity of Methanolic Extracts of Ayurvedic Medicinal Plants Used for Cognitive Disorders," PLoS One 9(1), e86804, Jan. 2014, 7 pages.
Government of India, Biological Diversity Act, 2002, India.†

\* cited by examiner
† cited by third party

*Primary Examiner* — Qiuwen Mi
(74) *Attorney, Agent, or Firm* — Christensen O'Connor Johnson Kindness PLLC

(57) ABSTRACT

The invention relates to the use of a composition from a plant extract of *Withania somnifera*, to treat or prevent amyloid-related diseases, including Alzheimer disease.

18 Claims, 9 Drawing Sheets

USE OF A *WITHANIA* EXTRACT FOR THE TREATMENT OF AMYLOID-RELATED DISEASES

Figure 1:
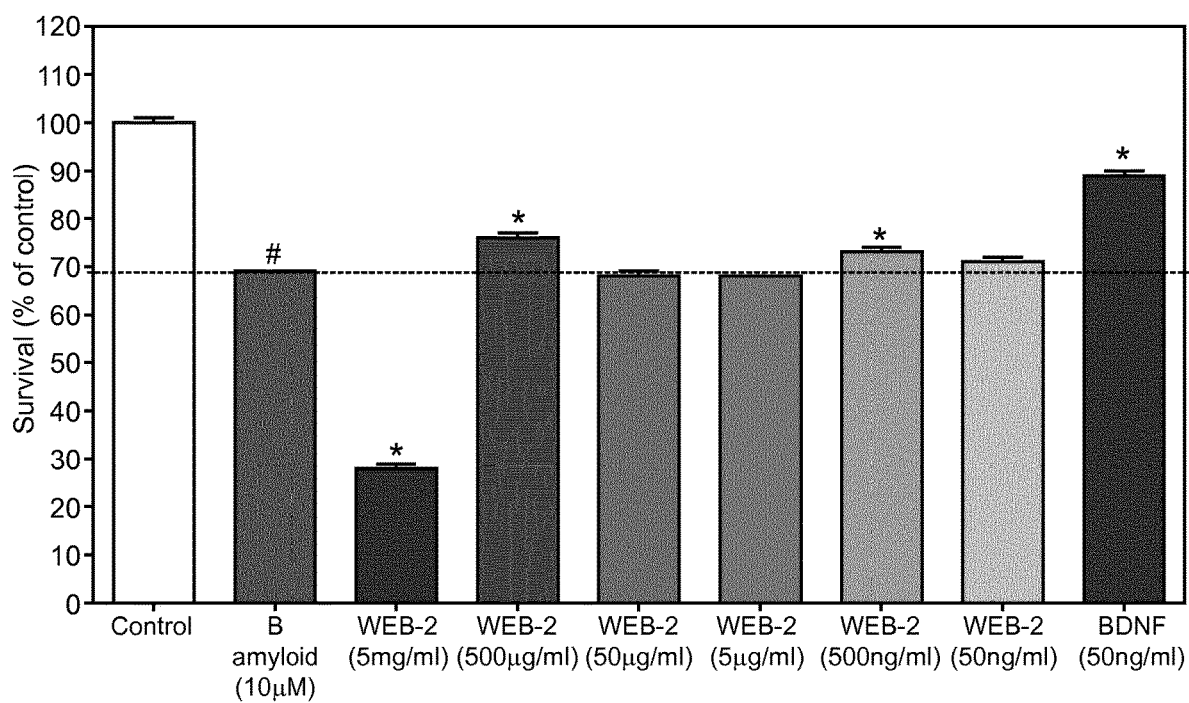

The invention relates to the use of a composition from a plant extract of *Withania somnifera*, to treat or prevent amyloid-related diseases, including Alzheimer disease.

Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties, stain with specific dyes (e. g., Congo red), and have a characteristic red-green birefringent appearance in polarized light after staining. They also share common ultrastructural features and common X-ray diffraction and infrared spectra. Amyloid-related diseases can either be restricted to one organ or spread to several organs. Once these amyloids have formed, there is no known, widely accepted therapy or treatment which significantly dissolves amyloid deposits in situ, prevents further amyloid deposition or prevents the initiation of amyloid deposition.

Alzheimer's disease (AD) is a degenerative central nervous system disorder associated with extensive loss of specific neuronal cells, and characterized clinically by progressive loss of memory, cognition, reasoning, judgment and emotional stability that gradually leads to profound mental deterioration and ultimately death. People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals and activated microglia.

AD affects mainly people over the age of 65 years, and as many as four million individuals in the United States alone. To date, there is no treatment that stops or reverses the disease and it presently causes up to 100,000 deaths annually.

AD is characterized by excessive production of small hydrophobic peptides called amyloid beta peptides (Aβ peptides) with Aβ42 peptide being particularly neurotoxic leading to pathogenesis of this disease. The brains of individuals with AD exhibit neuronal degeneration and characteristic lesions variously referred to as amyloid plaques and neurofibrillary tangles. Currently, the only definitive diagnosis of AD is the presence of these plaques in post-mortem brains. In specific cases, amyloid fibrils, once deposited, can become toxic to the surrounding cells. For example, these fibrils organized as senile plaques have been shown to be associated with dead neuronal cells, dystrophic neurites, astrocytosis, and microgliosis in patients with AD. When tested in vitro, oligomeric (soluble) as well as fibrillar peptide was shown to be capable of triggering an activation process of microglia (brain macrophages), which would explain the presence of microgliosis and brain inflammation found in the brain of patients with AD. Both oligomeric and fibrillar peptides can also induce neuronal cell death in vitro (M P Lambert, et al., Proc. Natl. Acad. Sci. USA 95, 6448-53 (1998)).

According to the dominant scientific hypothesis for AD, called amyloid cascade or amyloid hypothesis, it is believed that progressive cerebral deposition of particular amyloidogenic peptides, beta-amyloid peptides (Aβ peptides), play a detrimental role in the pathogenesis of AD and can precede cognitive symptoms and onset of dementia by years or possibly even decades (Hardy J, & Selkoe D J, Science. (2002) 297 (5580): 353-6).

Thus prevention of production of these peptides has become the major focus of pharmaceutical industry approaches to treatment of AD. The Aβ peptides are produced as a result of excessive processing of the amyloid precursor protein (APP), the parent trans-membrane protein found in neurons and other cells (Selkoe, D J. Trends Cell Biol. 1998, 8(11):447-53). Amyloid plaques are composed primarily of 40 and 42 amino acid peptides (called Aβ40 and Aβ42, respectively) derived from amyloid precursor protein (APP) by sequential proteolysis catalyzed by the aspartyl protease, beta-secretase, followed by presenilin-dependent gamma-secretase cleavage. Aβ42 is more hydrophobic and less soluble than Aβ40 and is the predominant species in amyloid plaques. Aβ42 is more prone to aggregation and deposition and therefore the cause of neurotoxicity as well as synaptic loss (Callizot N, et al., 2013. J Neurosci Res. 91: 706-16).

The mechanism by which Aβ peptides induce the neuronal cell death is not clear. However, numerous mechanisms such as intracellular calcium accumulation, reactive oxygen species (ROS) and nitric oxide (NO) productions, alteration of the cytoskeleton and nucleus and inflammatory processes that converge to the ubiquitous pathways of necrosis or apoptosis have been proposed. Since the AD brain is characterized by an ongoing chronic inflammatory process, research is directed at finding the root of this inflammatory response. Neurofibrillary tangles and senile plaques (aggregates mainly formed by amyloid beta peptide) are two landmark lesions in Alzheimer's disease. It has been documented that these oligomeric forms of Aβ interact with receptors from the glutamatergic system such as the NMDA-receptors, which are responsible for maintaining glutamate homeostasis (Campos-Peña. V. & M. A. Meraz-Ríos, 2014 Neurochemistry, Dr. Thomas Heinbockel (Ed.), ISBN: 978-953-51-1237-2, InTech, DOI: 10.5772/57367).

Many studies suggest that additionally to Aβ, NMDA receptors have a major role in the processes of learning and memory. Synaptic plasticity can be regulated positively or negatively, depending on the levels and degrees of amyloid oligomerization. The negative effect of these oligomeric forms may be reversed by the presence of NMDA receptor antagonists. In this regard, it has been reported that the noncompetitive antagonist memantine (NMDA receptor antagonist) is able to block the "pathological" receptor activation exerted by these oligomers (Kelly et al., 2006 J. Biol. Chem. 281, 28079-28089; Parsons et al., 2007, Neuropharmacology 53, 699-723, Costa R. O, et al., 2012. Aging Cell. 11(5):823-33).

In this view, an early pharmacological treatment with substances reducing the glutamate overstimulation might represent a very good option for the treatment of patients with AD.

Another type of amyloidosis is cerebral amyloid angiopathy (CAA). CAA is the specific deposition of amyloid-P fibrils in the walls of leptomeningeal and cortical arteries, arterioles and veins. It is commonly associated with AD, Down's syndrome and normal aging, as well as with a variety of familial conditions related to stroke or dementia (Frangione et al., Amyloid: J. Protein Folding Disord. 8, Suppl. 1, 36-42 (2001)).

Present therapies treat one or more symptoms of AD, including memory loss that disrupts daily life; challenges in planning or solving problems, difficulty completing familiar tasks at home, at work or at leisure, confusion with time or place, trouble understanding visual images and spatial relationships, new problems with words in speaking or writing, misplacing things and losing the ability to retrace steps, decreased or poor judgment, withdrawal from work or social activities, changes in mood and personality.

Presently available therapies for treatment of amyloid diseases are almost entirely symptomatic, and no comprehensive pharmacological therapy is currently available for the prevention or treatment of, for example, Alzheimer's disease (Roberson, E. D. & Mucke, L. (2006). Science, 314, 781-784).

Studies have shown a correlation between soluble Aβ levels and the extent of synaptic loss/severity of cognitive impairment (Mucke, L., et al., (2000) J Neurosci; 20:4050). Therefore, any substances reducing Aβ neurotoxicity may be useful as a new therapeutic agent for the treatment or prevention of amyloid-related diseases and in particular AD.

It has been reported that extracts of *Withania somnifera*, *Emblica officinalis* and *Bacopa monnieri* show anti-angiogenic activity. However, the extracts of these plants were not used because of the high toxicity related to the obtaining of the extracts and, in particular, the extract from *Withania somnifera*.

Surprisingly, the applicant has found that, by affecting the toxicity of the extracts of the plant *Withania somnifera*, by combining an extraction step and a fermentation step using filamentous fungi, it is possible to use the detoxified extract to treat AD and other neurodegenerative disorders.

The purpose of the invention is therefore to use a non-toxic composition based on extracts of *Withania somnifera*, having a protective effect against Aβ neurotoxicity to treat or prevent amyloid-related diseases.

Other objects, features, aspects and advantages of the invention will appear more clearly on reading the description and examples that follow:

FIG. 1: Effect of Aβ1-42 (10 μM, 24 hours) in presence or absence of WEB-2 plant extract or BDNF (50 ng/mL) on cell survival of primary cortical culture. Data were expressed in percentage of control conditions (no Aβ1-42=100%). All values were expressed as mean+/− SEM (s.e.mean) of the 6 wells. The results have been statistically analysed by ANOVA followed by Dunnett's test when allowed, using GraphPad Prism software (GraphPad, United States). # $p<0.05$ Control vs B amyloid group; * $p<0.05$ vs B amyloid group.

Figure 2A:
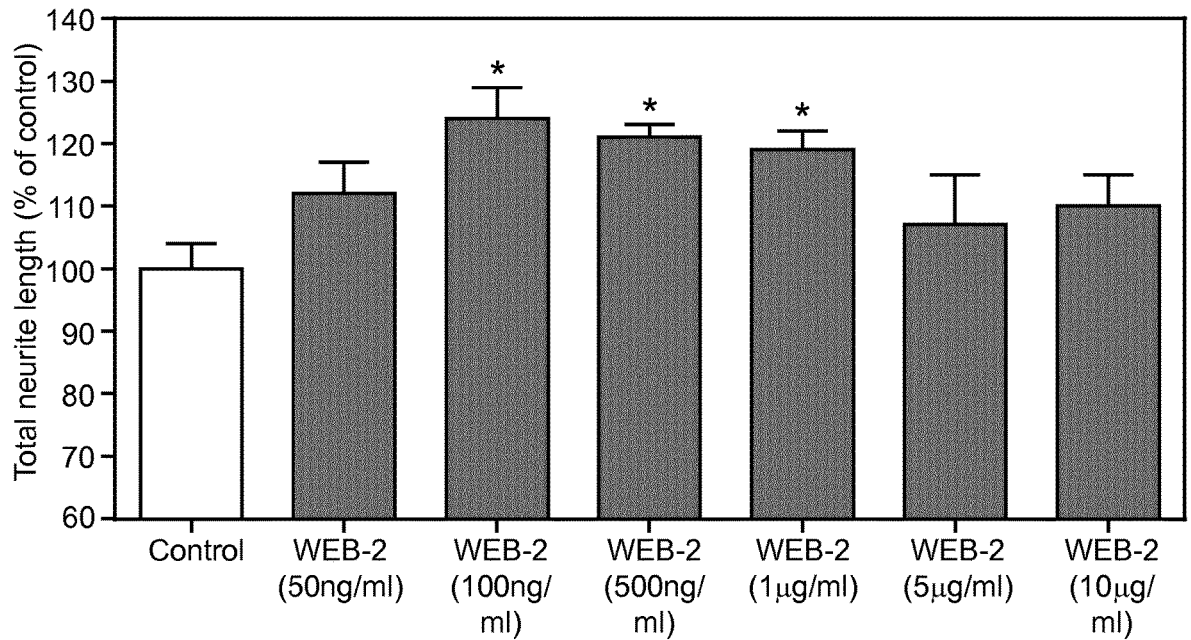
Figure 2B:
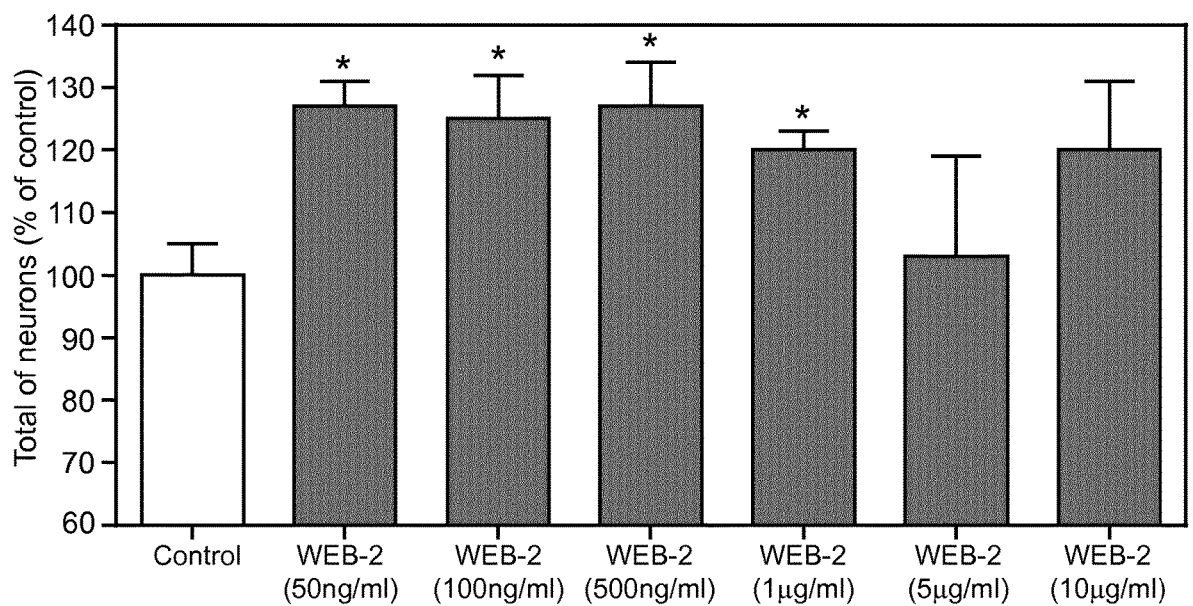

FIG. 2: Effect of WEB-2 Plant extract at different concentrations on neurite network (2a) and neuron survival (2b) after 3 days of treatment. Data were expressed as percentage of control as mean±SEM (100%=no plant extract). # $p<0.05$ vs control condition (one way ANOVA followed by PLSD Fisher's test.

Figure 3A:
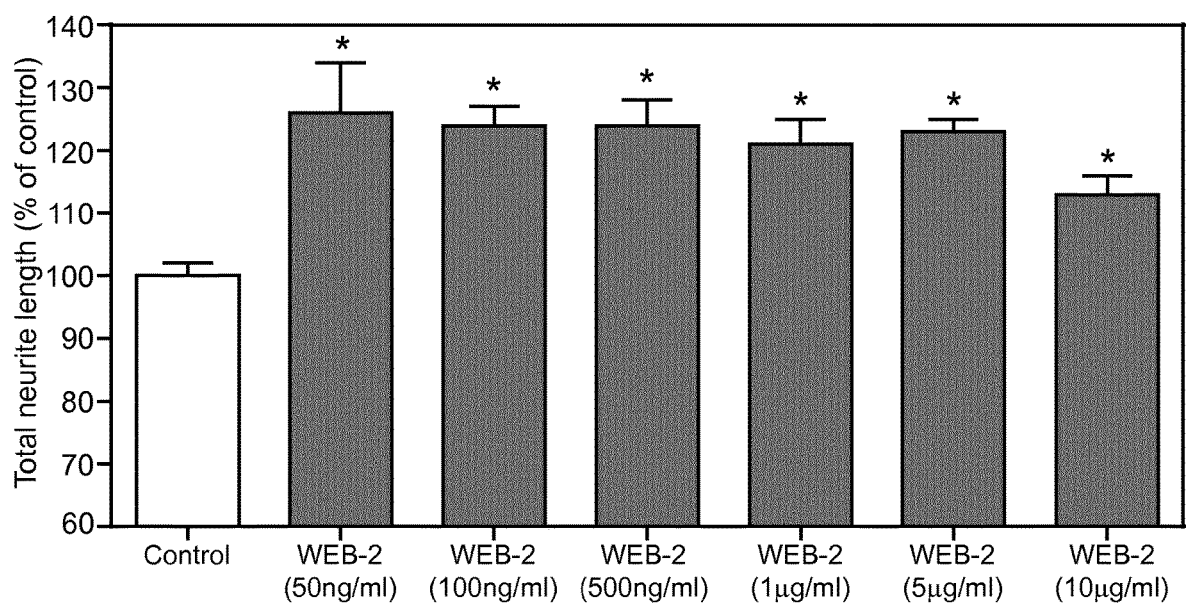
Figure 3B:
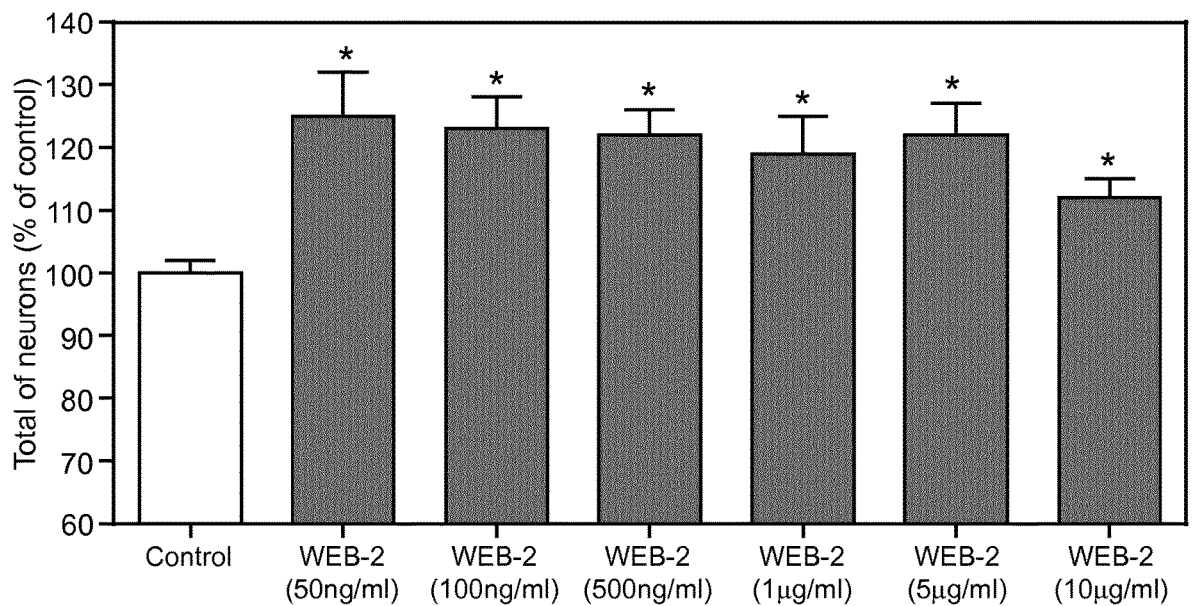

FIG. 3: Effect of WEB-2 at different concentrations on neurite network (3a) and neuron survival (3b) after 5 days of treatment. Data were expressed as percentage of control as mean±SEM (100%=no plant extract). # $p<0.05$ vs control condition (one way ANOVA followed by PLSD Fisher's test.

Figure 4A:
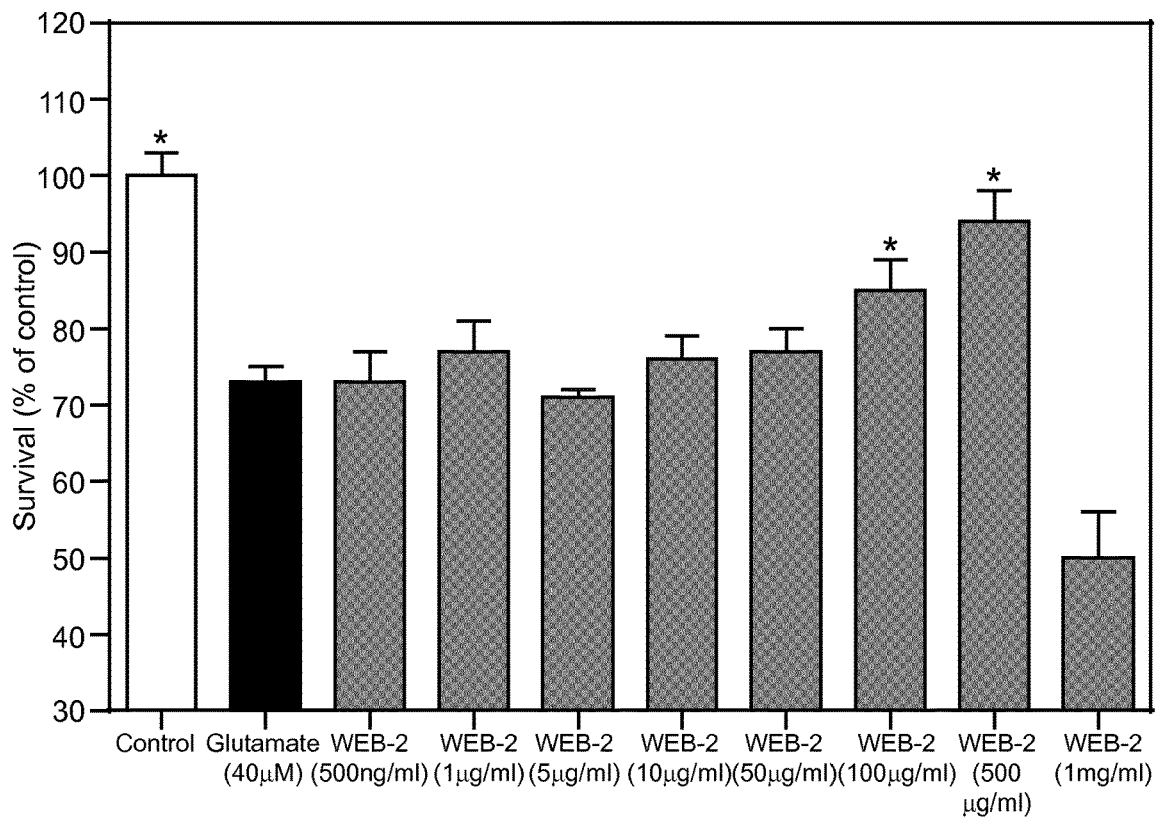
Figure 4B:
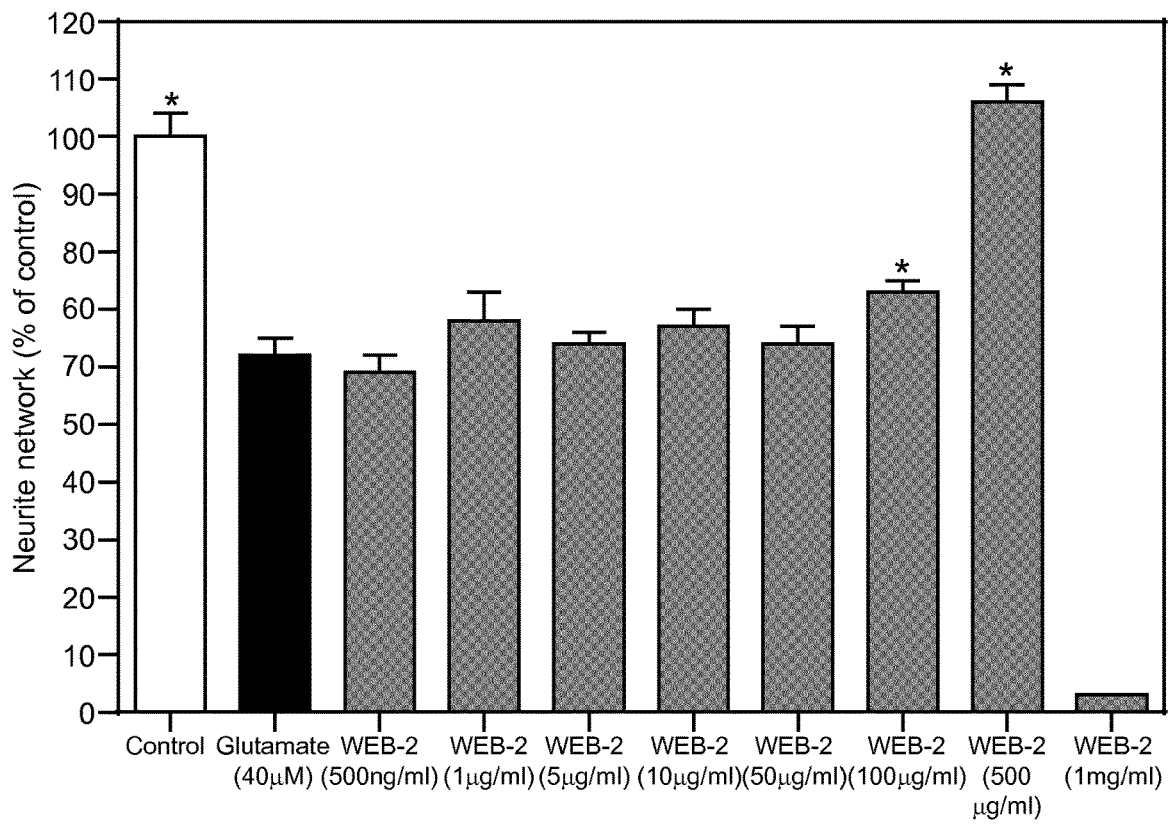

FIG. 4: Effect of glutamate (40 μM, 20 min) on neuron survival (4a) and neurite network (4b) of primary cortical culture in presence or absence of WEB-2 pretreatment during one hour. Data were expressed as percentage of control as mean±SEM (100%=no glutamate). * $p<0.05$ vs glutamate condition (one way ANOVA followed by PLSD Fisher's test).

Figure 5A:
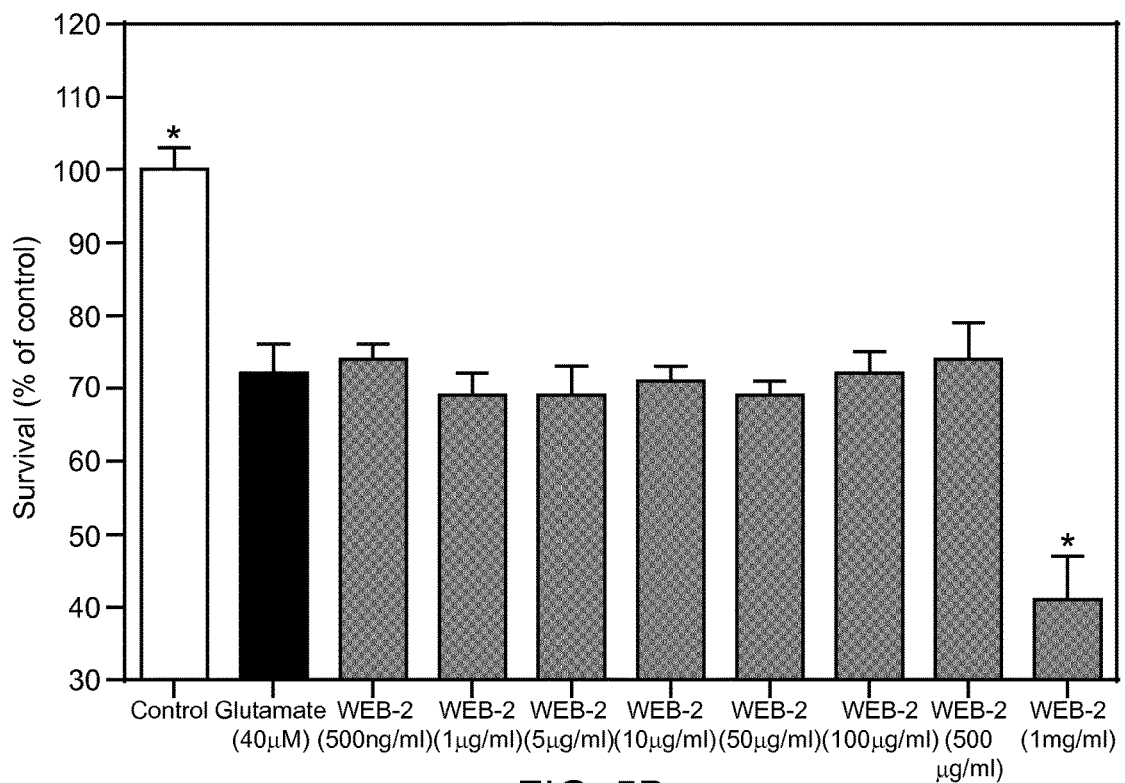
Figure 5B:
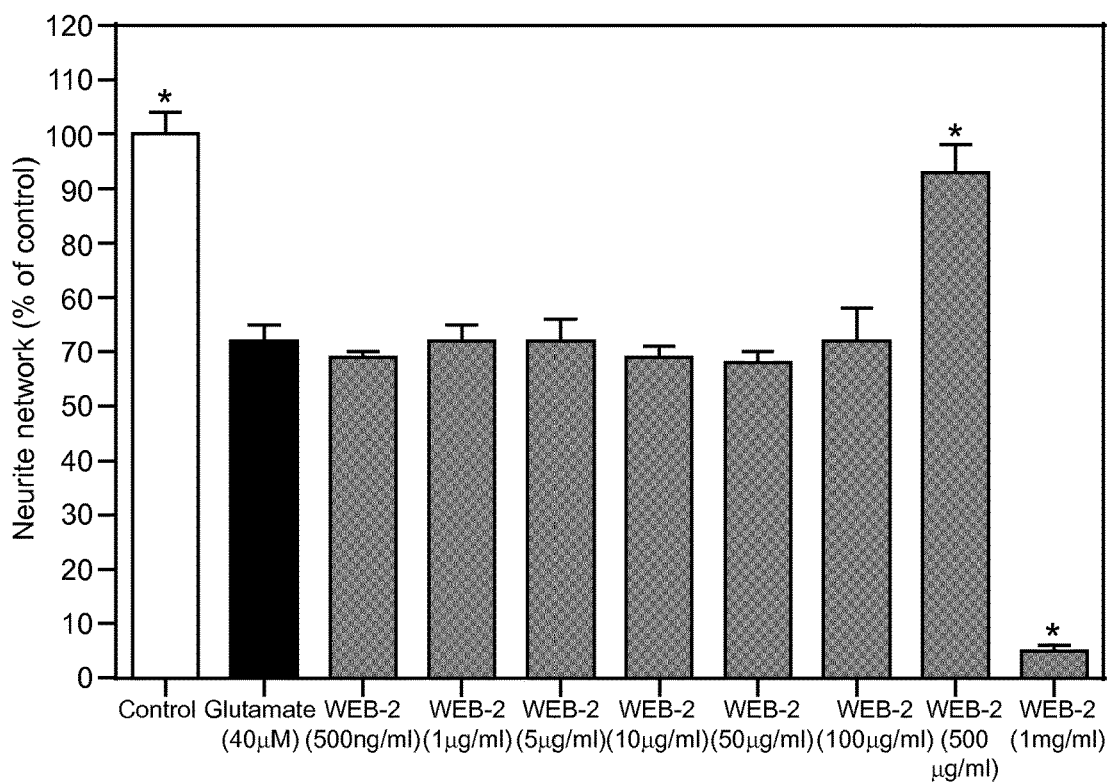

FIG. 5: Effect of glutamate (40 μM, 20 min) on neuron survival (5a) and neurite network (5b) of primary cortical culture in presence or absence of WEB-2 in co-treatment with the glutamate. Data were expressed as percentage of control as mean±SEM (100%=no glutamate). * $p<0.05$ vs glutamate condition (one way ANOVA followed by PLSD Fisher's test).

Figure 6A:
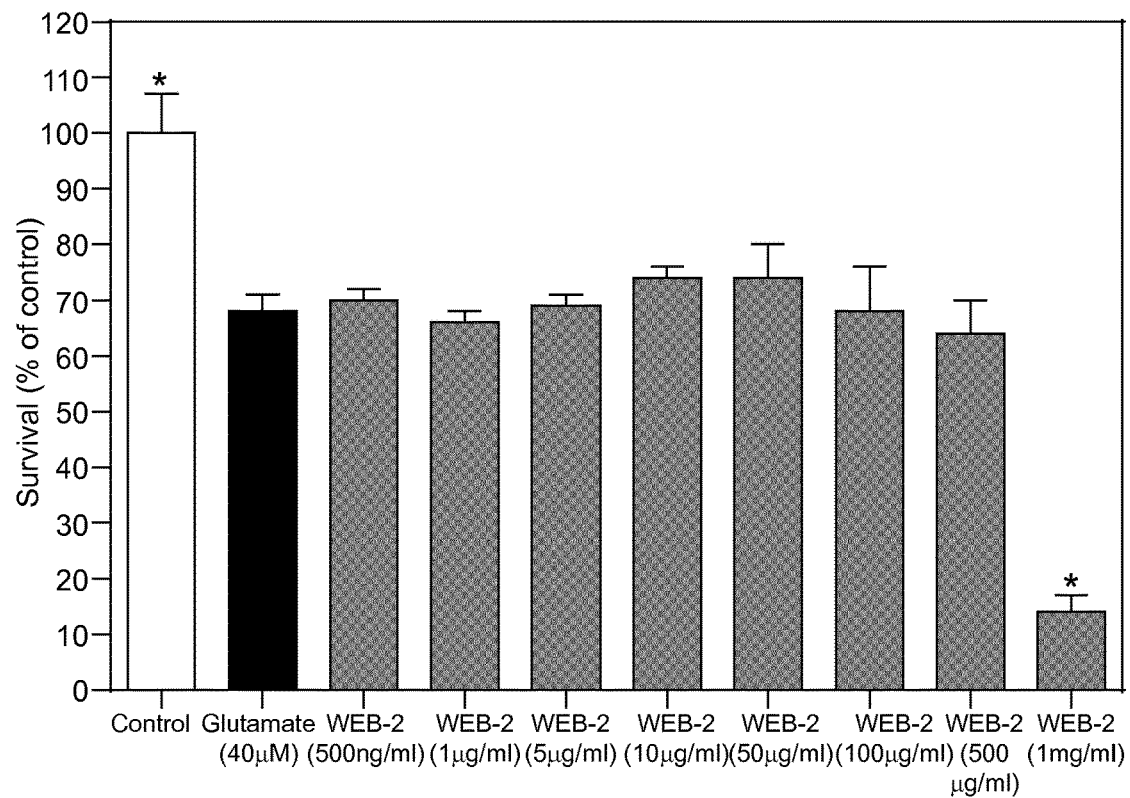
Figure 6B:
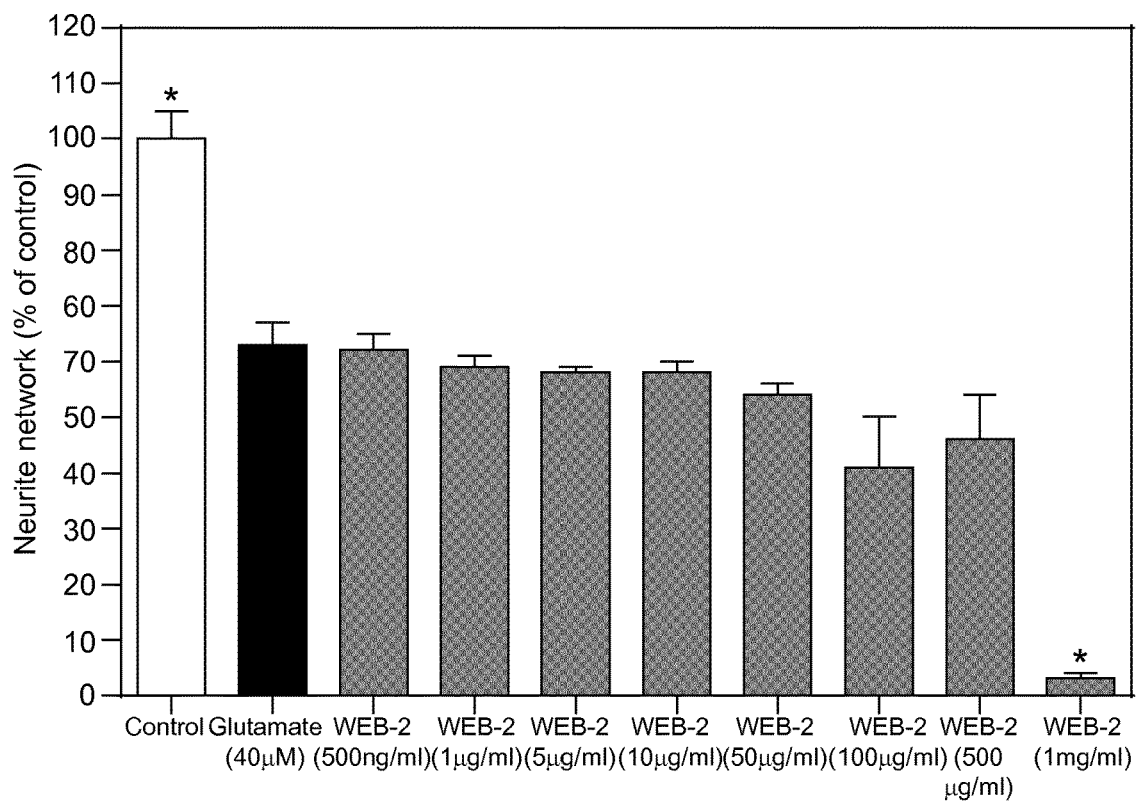

FIG. 6: Effect of glutamate (40 μM, 20 min) on neuron survival (6a) and neurite network (6b) of primary cortical culture in presence or absence of WEB-2 treatment four hours after glutamate treatment. Data were expressed as percentage of control as mean±SEM (100%=no glutamate). * $p<0.05$ vs glutamate condition (one way ANOVA followed by PLSD Fisher's test).

FIG. 7: Effect of WEB-1 (different concentration) on neurite network (7a) and neuron survival (7b) after 3 days of treatment. Data were expressed as percentage of control as mean±SEM (100%=no plant extract)*$p<0.05$ (one way ANOVA followed by PLSD Fisher's test).

FIG. 8: Effect of WE-2 (different concentration) on neurite network (8a) and neuron survival (8b) after 3 days of treatment. Data were expressed as percentage of control as mean±SEM (100%=no plant extract). * $p<0.05$ (one way ANOVA followed by PLSD Fisher's test).

Figure 9A:
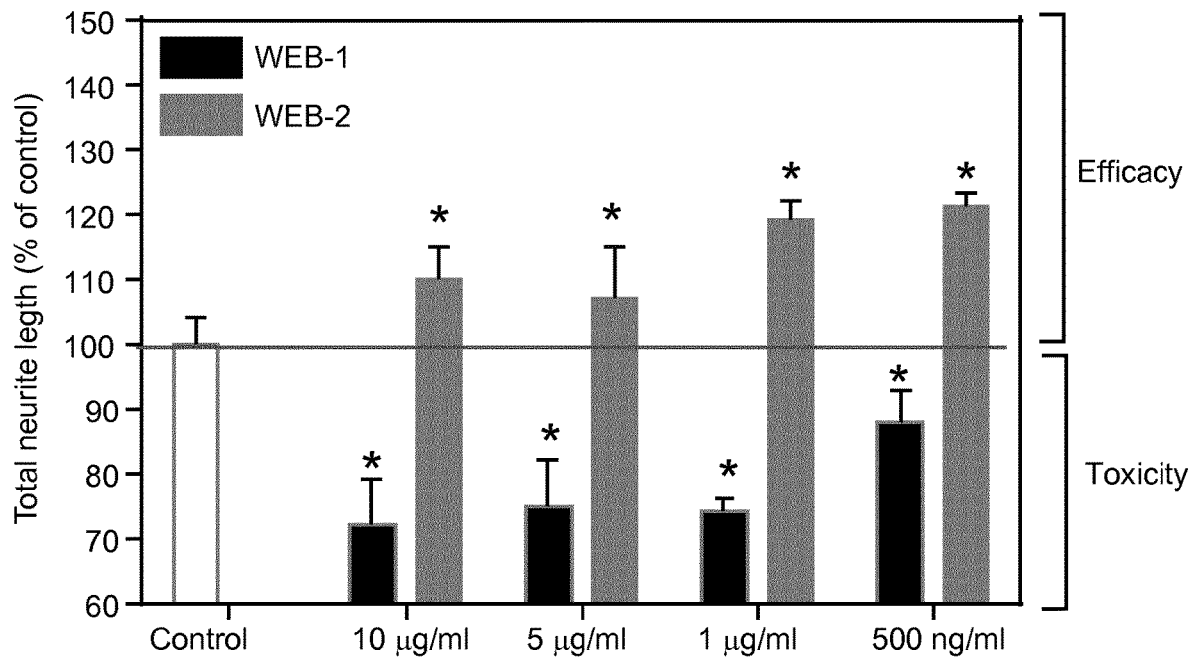

FIG. 9A: Comparison between WEB-1 and WEB-2 (different concentrations) on total neurite length.

Figure 9B:
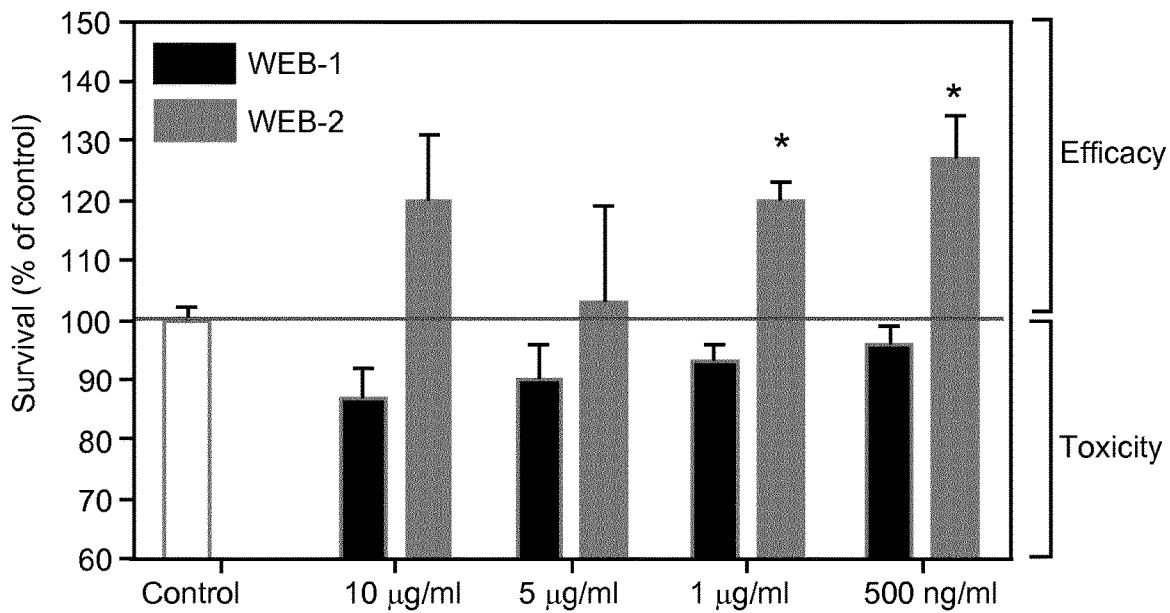

FIG. 9B: Comparison between WEB-1 and WEB-2 (different concentrations) on total neuronal survival.

The invention is directed to the use of a composition containing a *Withania somnifera* extract for its use to treat or prevent amyloid-related diseases in a mammal. Preferably, the mammal is a human.

Preferably, the *Withania somnifera* extract has been fermented by its incubation with a filamentous fungus in a suitable environment.

The *Withania somnifera* plant is obtained from India. The root of this plant is marketed by Alp Erbo (Marseille).

The process of production of extracts according to the invention can be found in WO 2014/202469. Briefly, the plants are fermented in presence of a filamentous fungus of the family Cordycipitaceae, preferably the genus *Beauveria*. More preferably, the filamentous fungus is derived from the strain *Beauveria bassiana*, more particularly the strain having reference ATCC 7159.

The controlled fermentation detoxifies the *Withania Somnifera* extract by a series of biocatalysis of various molecules contained in this extract and, more particularly, the chemical family of withanolide aglycones, the substances mainly responsible for the toxicity of the extract.

The term "detoxification" is used to mean elimination by the microorganism of potentially toxic molecules in the medium.

Preferably, after the fermentation, filtration, the medium is then subjected to sterilisation steps, preferably by ultrafiltration, in order to obtain the solution which constitutes the plant extract.

The plant extract of the invention contain *Withania somnifera* but may also contain at least one of the following extracts *Emblica officinalis*, originating in India and marketed by Infrag, Bengalore), *Bacopa monnieri* (India) marketed by Alp Erbo (Marseille), *Punica granatum* (China) (Shanghai Brightol International Co, Ltd (Shanghai), *Curcuma longa* (India) (Omnipharm, Chambery), *Piper longum* (Thailand) (Omnipharm, Chambery), or *Calendula officinalis* (China) (Shanghai Brightol International Co, Ltd (Shanghai), using the same procedure), by independent extraction steps for each plant extract used in the realisation of the said preparation.

Advantageously, the composition used in this invention includes, by weight, between 5 and 100 g/L of *Withania somnifera*, preferably 20 g/L. Preferentially, this composition also includes one of the following extracts, expressed by weight:

- between 5 and 100 g/L of *Emblica officinalis*, preferably 15 g/L,
- between 5 and 100 g/L of *Bacopa monnieri*, preferably 15 g/L,
- between 5 and 50 g/L of *Punica granatum*, preferably 10 g/L,
- between 5 and 250 g/L of *Curcuma longa*, preferably 20 g/L,
- between 20 and 50 mg/L of *Piper longum*, preferably 30 mg/L,
- between 5 and 50 g/L of *Calendula officinalis*, preferably 10 g/L, Preferably, the composition used in this invention comprises an extract of the plants *Withania somnifera*, *Emblica officinalis* and *Bacopa monnieri*. More preferably, the composition according to the invention comprises a quantity by weight of *Withania somnifera* at a concentration of 20 g/L, of *Emblica officinalis* at a concentration of 15 g/L and of *Bacopa monnieri* at a concentration of 15 g/L.

The compositions according to the invention are used to treat or prevent Alzheimer's disease, cerebral amyloid angiopathy, inclusion body myositis, or Down's syndrome.

In certain embodiments of the invention, the methods and compositions reduce the progression of AD in particular, and in some embodiments the methods and compositions of the invention are effective to treat a larger spectrum of AD patients. In certain cases the invention is effective for individuals having early onset or familial AD.

In some embodiments, there is a method of treating a amyloid-related disease in an individual, comprising the step of delivering to the individual a therapeutic amount of a plant extract composition, such that said amyloid-related disease in a subject is treated or prevented, wherein said composition contains a plant extract of *Withania somnifera*.

The amyloid-related diseases comprise Alzheimer's disease, cerebral amyloid angiopathy, inclusion body myositis or Down's syndrome.

In some embodiments, the method of use of the composition of the invention is intended to reduce or inhibit amyloid fibril formation or deposition, neurodegeneration, or cellular toxicity is reduced or inhibited.

The use of the composition of the invention causes in an Alzheimer's patient a stabilization of cognitive function, prevention of a further decline in cognitive function, or prevention, slowing, or stopping of disease progression.

The composition according to the invention is formulated for oral or parenteral administration.

A person skilled in the art of pharmaceutical formulation will implement the various useful forms for administration of the compositions and/or supplements of the invention. The compositions may be in liquid, gel, emulsion, solid or injectable form.

The composition used may additionally include suspensions, emulsions, syrups containing conventionally used inert diluents, and possibly other substances such as wetting agents, sweeteners, preservatives, thickeners, colourings or any other substance known to a person skilled in the art suitable for oral administration, in particular ((sodium sorbate (E201) (Sigma-Aldrich), anthocyanin (E163) (FBC Industries, USA), sodium metabisulphite (E223) (Sigma-Aldrich), alpha-tocopherol (E307) (FBC Industries, USA).

The composition used may also comprise solvents or other excipients such as water, propylene glycol, vegetable oils or other suitable organic solvents.

The term "excipient" is used to mean any compound which does not interfere with the effectiveness of the biological activity of the composition according to the invention, and which is not toxic to the host to which it is administered.

The composition used may also contain adjuvants, such as wetting agents, isotoning agents, emulsifiers, salts or any other substances known to a person skilled in the art that can be used as adjuvants (Polydimethylsiloxane, polyvinyl alcohol (PVA), hydrogels (Carbopol), polyvinylpyrrolidone, hydroxypropyl cellulose (HPC), poloxamer 188, EDTA, chlorobutanol) (Lubrizol, France, Dow Corning, USA).

Advantageously, the composition may comprise other substances such as vitamins, mineral salts, a pharmaceutically acceptable vector, stabilisers, antioxidants, or any other substance known to a person skilled in the art and intended to be integrated into a drug.

Preferably, the composition is liquid, orally administrable and contains at least a non-toxic extract of *Whitania somnifera*, some preservatives, vitamins, water and salt.

More preferably, the preservatives are potassium sorbate or benzoate. The vitamin may be riboflavin (vitamin B2).

The therapeutic composition used in the method of the invention is administered in a pharmaceutically acceptable vehicle.

The terms "pharmaceutically acceptable vehicle" is used to mean any vehicle which does not interfere with the effectiveness of the biological activity of the composition according to the invention and which is not toxic to the host to which it is administered.

The composition obtained is usable as a medicinal product for a mammal, and more particularly for humans, to assist in the treatment or prevention of disorders or diseases linked to amyloidal-related diseases and in particular AD.

The term "medicinal product" is used to mean a product containing an accurate dose of said preparation according to European directive 65/65/EC, namely any substance or composition described as possessing curative or preventive properties with respect of human or animal disease. For example, the medicinal product containing said preparation at therapeutic doses can be administered orally as a capsule or a tablet, or injected via any other route to confer the beneficial effects.

An appropriate dosage of the therapeutic composition can be determined by one of skill in the art, taking into consideration the findings described herein together with typical factors such as the body mass of the patient, the physical condition of the patient, and so on. The dosage should contain the therapeutic composition in an amount that is effective for treating amyloid-related diseases, including AD.

The drug can be administered daily, weekly, or on an intermittent basis. For example, the drug can be administered for three weeks on, followed by one week off, or for two weeks on, followed by one week off, or under other dosing schedules as can be determined by one skilled in the field.

The particular dose selected will depend upon the mode of administration and dosing regimen selected. One preferred schedule is a once daily oral dosing schedule. When longer periods of time are prescribed between each application (typically the case for i.v administration), each unit dose may be larger than when daily dosages are provided.

The daily dose of the compositions used may vary according to the needs and severity of symptoms of the patient and according to the route. Typically, the daily dose is between 10 mg/mL and 300 mg/mL of the solution after fermentation.

Preferably, the daily dose for an adult human is between 30 and 100 mg/mL of the solution after fermentation.

The present invention will be explained in further detail by way of non-limiting examples below, which make reference to the appended drawings. The following methods were used in the experiments described in the examples that follow the description of the methods.

EXAMPLE 1: COMPOSITION WEB-1 BEFORE FERMENTATION

The composition WEB-1 contains a commercial extract of *Withania Somnifera* at a concentration of 20 g/L, of *Emblica officinalis* at a concentration of 15 g/L, of *Bacopa monnieri* at a concentration of 15 g/L.

A solution of 100 mL is made in water. After lyophilization, 3.8 g of a beige powder is obtained.

EXAMPLE 2: STRAIN OF FILAMENTOUS FUNGUS *BEAUVERIA BASSIANA*

The strain Beauvaria Bassiana (reference ATCC 7159) has been cultivated in a medium containing 0.5 g/L $KH_2PO_4$; 1 g/L $KH_2PO_4$; 1 g/L $MgSO_4$; 2 g/L $NaNO_3$; 0.5 g/L KCl; 0.02 g/L $FeSO_4$; 30 g/L glucose (all reagents from Sigma-Aldrich, France) and 10 g/L of corn steep liquor (Roquette, France).

The culture was then agitated at 200 rotations per minute, for 72 hours at 27° C. It was then filtered by non-sterile methods on a filter paper to separate the fungal biomass from the culture medium. The fungal biomass was then washed thoroughly with water.

EXAMPLE 3: COMPOSITION WEB-2 USED IN THE INVENTION

The composition WEB-1 as in example 1 is added to the fresh fungal biomass of example 2 using 60 g of biomass per liter of composition WEB-1 containing 50 g of glucose.

After incubation, this seeded composition was agitated at 200 rpm for 5 days at a temperature of 27° C.

After 5 days, the incubation medium was filtered on a filter paper, the samples for HPLC assay were also filtered using a 0.45 micron filter (Ait-France, ref: SFNY 013045N).

The brownish solution obtained which was then lyophilized during 5 days to produce dried beige powder.

EXAMPLE 4: COMPOSITION WE-2 USED IN THE INVENTION

The composition WE-1 contains an commercial extract of *Withania Somnifera* at a concentration of 20 g/L, and of *Emblica officinalis* at a concentration of 15 g/L.

To 100 mL of such a solution, are added 5 g of glucose and 6 g of biomass of example 2.

After having treated and lyophilized the solution like in example 3, 4.13 g of a beige powder is obtained.

The markers identified in the composition WE-2 were Withanoside IV, Withanoside VI and gallic acid.

EXAMPLE 5: COMPOSITION WB-2 USED IN THE INVENTION

The composition WB-1 contains an extract of *Withania Somnifera* at a concentration of 20 g/L, and of *Bacopa Monnieri* at a concentration of 15 g/L.

To 100 mL of such a solution, are added 5 g of glucose and 6 g of biomass of example 2.

After having treated and lyophilized the solution like in example 3, 2.62 g of a beige powder is obtained.

The markers identified in the composition WB-2 were Withanoside IV, Withanoside VI, Bacoside A3, Bacopaside X and Bacopasaponin C.

EXAMPLE 6: COMPOSITION BE-2 USED IN THE INVENTION

The composition BE-2 contains an extract of *Bacopa Monnieri* at a concentration of 15 g/L, and of *Emblica officinalis* at a concentration of 15 g/L.

To 100 mL of such a solution, are added 5 g of glucose and 6 g of biomass of example 2.

After having treated and lyophilized the solution like in example 3, 2.62 g of a beige powder is obtained.

The markers identified in the composition BE-2 were Bacopaside X, Bacopasaponin C and gallic acid.

EXAMPLE 7: COMPOSITION WEB-4 ACCORDING TO THE INVENTION

The composition WBE-4 contains an extract of *Withania Somnifera* at a concentration of 40 g/L, of *Bacopa Monnieri* at a concentration of 15 g/L, and of *Emblica officinalis* at a concentration of 15 g/L.

To 100 mL of such a solution, are added 5 g of glucose and 6 g of biomass of example 2.

After having treated and lyophilized the solution like in example 3, 4.23 g of a beige powder is obtained.

EXAMPLE 8: COMPOSITION WEB-6 USED IN THE INVENTION

The composition WEB-6 contains an extract of *Withania Somnifera* at a concentration of 20 g/L, of *Bacopa Monnieri* at a concentration of 15 g/L, and of *Emblica officinalis* at a concentration of 30 g/L.

To 100 mL of such a solution, are added 5 g of glucose and 6 g of biomass of example 2.

After having treated and lyophilized the solution like in example 3, 4.22 g of a beige powder is obtained.

EXAMPLE 9: COMPOSITION WEB-8 USED IN THE INVENTION

The composition WEB-8 contains an extract of *Withania Somnifera* at a concentration of 20 g/L, of *Bacopa Monnieri* at a concentration of 30 g/L, and of *Emblica officinalis* at a concentration of 15 g/L.

To 100 mL of such a solution, are added 5 g of glucose and 6 g of biomass of example 2.

After having treated and lyophilized the solution like in example 3, 3.76 g of a beige powder is obtained.

EXAMPLE 10: NEUROPROTECTIVE EFFECT ON AN IN VITRO MODEL OF ALZHEIMER DISEASE

The brains of Alzheimer's disease patients have large numbers of plaques (extracellular deposits) that contain amyloid beta (Aβ) peptides which are believed to play a pivotal role in AD pathology. These peptides contribute to cerebrovascular lesions and are neurotoxic. This study investigated the neuroprotective effect of the plant extract of the invention on rat primary cortical cultures following exposure to Aβ1-42 in an in vitro AD model (Callizot. N., et al., 2013).

a) Culture of Cortical Neurons

Rat cortical neurons were cultured as described by Singer C. A., et al., 1999. J Neurosci 19: 2455-2463 and Callizot. N., et al., 2013 J Neurosci Res. 91: 706-16.

Briefly, pregnant Wistar females (Janvier Labs, France) at 15 days of gestation were killed by cervical dislocation. Foetuses were collected and immediately placed in ice-cold L15 Leibovitz medium (Batch: 4290114, Pan Biotech, Germany) with a 2% penicillin (10,000 U/mL) and streptomycin (10 mg/mL) solution (PS Batch: 7500912; Pan Biotech) and 1% bovine serum albumin (BSA Batch: K030913; Pan Biotech). Cortex was treated for 20 min at 37° C. with a trypsin-EDTA solution (Batch: 7310713, Pan Biotech,) at a final concentration of 0.05% trypsin and 0.02% EDTA. The dissociation was stopped by addition of Dulbecco's modified Eagle's medium (DMEM) with 4.5 g/L of glucose (Batch: 9710913, Pan Biotech,), containing DNAse I grade II at the final concentration of 0.5 mg/mL (Batch: H131108, Pan Biotech,) and 10% fetal calf serum (Batch: 41Q7218K, Invitrogen, France). Cells were mechanically dissociated by three forced passages through the tip of a 10-mL pipette. Cells were then centrifuged at 515 g for 10 min at 4° C. The supernatant was discarded, and the pellet was resuspended in a defined culture medium consisting of Neurobasal medium (Batch: 1576979, Invitrogen) with a 2% solution of B27 supplement (Batch: 1589889, Invitrogen), 2 mmol/L of L-glutamine (Batch: 5030513, Pan Biotech,), 2% of PS solution, and 10 ng/mL of brain-derived neurotrophic factor (BDNF) (Batch: H140108, Pan Biotech). Viable cells were counted in a Neubauer cytometer, using the trypan blue exclusion test. The cells were then seeded at a density of 30,000 per well in 96-well plates precoated with poly-L-lysine (Batch: 3102256, Corning Biocoat, United States) and were cultured at 37° C. in an air (95%)-$CO_2$ (5%) incubator in B27 medium. The medium was changed every 2 days. The cortical neurons were intoxicated with amyloid beta peptides solutions after 11 days of culture.

b) Preparation of Solutions

The Amyloid beta peptide 1-42 (Aβ1-42) preparation was done following the procedure described by Callizot. N., et al., 2013 J Neurosci Res. 91: 706-16. Briefly, Aβ1-42 peptide (Batch: APN09080-1-1, Abcam, United Kingdom) was dissolved in the defined culture medium B27 mentioned above, devoid of serum, at an initial concentration of 40 µmol/L. This solution was gently agitated for 3 days at 37° C. in the dark and immediately used after being properly diluted in culture medium.

The plant extract WEB-2 of example 2 (5 mg/mL, 500, 50, 5 µg/mL, 500 and 50 ng/mL), and Brain Derived Neurotrophic Factor (BDNF, Sigma Aldrich France) (50 ng/mL) were solved or diluted in culture medium and then pre-incubated with primary cortical neurons in 96-wells plates at 6 wells per condition for 1 hour at room temperature Then Aβ1-42 preparation were added to a final concentration of 10 µM diluted either in control medium, or in presence of WEB-2 Plant extract at different concentrations or BDNF.

BDNF is known to act on certain neurons of the central nervous system and the peripheral nervous system, helping to support the survival of existing neurons, and encourage the growth and differentiation of new neurons and synapses.

c) Antibodies Labeling

After 24 hours, cells were fixed by a cold solution of ethanol 95% (Batch: SZBD1470V, Sigma) and acetic acid 5% (Batch: SZBD1760V, Sigma) for 5 min at −20° C. After permeabilization with 0.1% of saponin (Batch: BCBJ8417V, Sigma), cells were incubated for 2 h with:

1) Mouse monoclonal antibody anti microtubule-associated-protein 2 (MAP-2; Batch: 063M4802, Sigma) at dilution of 1/400 in PBS (Batch: 7750514, Pan biotech) containing 1% foetal calf serum (Batch: 41Q7218K, Invitrogen) and 0.1% of saponin at room temperature. This MAP-2 Ab specifically stained neurons.

2) Rabbit antibody anti Glial fibrillary acidic protein (GFAP) (Batch: 083M4830, Sigma) at dilution of 1/400 in PBS containing 1% foetal calf serum and 0.1% of saponin at room temperature. This antibody specifically stained cell bodies of glial cells allowing quantifying the cell death of these cells.

These 2 antibodies were revealed with Alexa Fluor 488 goat anti-mouse IgG (Batch: 1397999, Molecular probe, France) and Alexa Fluor 568 goat anti-rabbit IgG (Batch: 1180090, Molecular Probe) at the dilution of 1/400 in PBS containing 1% foetal calf serum and 0.1% of saponin for 1 H at room temperature.

d) Analysis of total number of cells (neuronal and glial cells)

The immunolabeled cultures were automatically examined with ImageXpress equipped with a LED at ×20 magnification (Molecular Devices, United Kingdom). For each condition (6 culture wells), 30 fields per well (representing ~80% of the total surface of the well) were analyzed. The total survival was automatically analyzed using MetaXpress software (Molecular Devices)

e) Results

The FIG. 1 shows the effect of the different components used on β-amyloid injuries.

The results show that Aβ1-42 (10 µM-24 h) induced a significant cell death (>30%) as previously shown in literature (Callizot et al., 2013). In presence of plant extract (500 µg/mL), a significant protective effect was observed. Interestingly, the neuroprotective effect was persisting at the lowest concentration (500 ng/mL). At the highest concentration (5 mg/mL), the plant extract showed a large toxic effect.

In this study, BNDF (50 ng/mL) is used as reference compound.

As a conclusion:

Aβ1-42 (10 µM-24 h) applied on primary cortical neuron culture induced a significant cell death as previously described.

Plant extract, tested at 500 µg/mL showed a clear and significantly neuro-protective effect on Aβ1-42 induced injuries.

The range of the most active doses seems to be around 500 µg/mL.

EXAMPLE 11: EFFECT OF ONE PLANT EXTRACT ON NEURITOGENESIS ON PRIMARY CORTICAL NEURONS

This study investigates the effect of the plant extract WEB-2 at different concentrations on neuritogenesis on primary cortical neuron culture. A chronic treatment was performed for 3 and 5 days and the effect on neurite outgrowth was assessed on these two time points.

a) Culture of Cortical Neurons

Rat cortical neurons were cultured as described by Singer C. A., et al., 1999. J Neurosci. 1999 April 1; 19(7):2455-63 and Callizot N., et al., 2013. J Neurosci Res. 2013 May; 91(5):706-16.

Briefly, foetuses were collected and immediately placed in ice-cold L15 Leibovitz medium (Pan Biotech) with a 2% penicillin (10,000 U/mL) and streptomycin (10 mg/mL) solution (PS; Pan Biotech, Batch: 1451013) and 1% bovine serum albumin (Batch: K180713, Pan Biotech). Cortex were treated for 20 min at 37° C. with a trypsin-EDTA (Batch: 7310713, Pan Biotech) solution at a final concentration of 0.05% trypsin and 0.02% EDTA. The dissociation was stopped by addition of Dulbecco's modified Eagle's medium (DMEM) with 4.5 g/L of glucose (Batch: 9710913, Pan Biotech), containing DNAse I grade II at a final concentration of 0.5 mg/mL; (Batch: H130919, Pan Biotech) and 10% fetal calf serum (Batch: 41Q7218K, Invitrogen). Cells were mechanically dissociated by three forced passages through the tip of a 10-mL pipette. Cells were then centrifuged at 515×g for 10 min at 4° C. The supernatant was discarded, and the pellet was resuspended in a defined culture medium consisting of Neurobasal medium (Batch: 1625353, Invitrogen) with a 2% solution of B27 supplement (Batch: 1618508, Invitrogen), 2 m mol/L of L-glutamine (Batch: 6620314, Pan Biotech), 2% of PS solution, and 10 ng/mL of brain-derived neurotrophic factor (Batch: H140108, Pan Biotech). Viable cells were counted in a Neubauer cytometer, using the trypan blue exclusion test. The cells were seeded at a density of 30,000 per well in 96-well plates precoated with poly-L-lysine (Batch: 3102256, Biocoat) and were cultured at 37° C. in an air (95%)-CO2 (5%) incubator. The medium was changed every 2 days. Cells were immediately incubated with or without plant extract.

b) Solutions of Plant Extract

The plant extract WEB-2 was solved in culture medium then pre-incubated with neurons after cell plating. The following concentrations were tested in the culture wells: 50, 100, 500 ng/mL, 1, 5, 10, 50, 100 and 500 µg/mL. The plant extract WEB-2 as well as BDNF (50 ng/mL) were tested in 96 well plates (6 wells per condition).

c) Neurite Outgrowth and Neuronal Survival Evaluation

On day 3 and 5 of culture, the cortical neurons were fixed by a cold solution of ethanol 95% Batch: SZBD1470V, Sigma) and acetic acid 5%, (Batch: SZBD1760V, Sigma) for 5 min. After permeabilization with 0.1% of saponin, cells were incubated for 2 hours with a monoclonal antibody anti microtubule-associated-protein 2 (Batch: 063M4802, Sigma) at dilution of 1/400 in PBS containing 1% foetal calf serum and 0.1% of saponin. This antibody stains specifically cell bodies and neurites of neurons (MAP-2) allowing study of neuron survival and neurite evaluation in the culture. A neurite refers to any projection from the cell body of a neuron.

This antibody was revealed with Alexa Fluor 488 goat anti-mouse IgG (Batch: 1397999, Molecular Probes) at the dilution of 1/400 in PBS containing 1% foetal calf serum and 0.1% of saponin for 1 hour at room temperature.

The immunolabeled cultures were automatically examined with ImageXpress (Molecular Devices) equipped with a LED at ×20 magnification. For each condition, 30 pictures (representing ~80% of the total surface of the well) per well were taken. All images were taken with the same conditions. Number of MAP-2 positive cells and neurites of MAP-2 positive cells were automatically analyzed by using Custom module editor (Molecular Devices). The total survival and neurite network was automatically analyzed using MetaXpress software (Molecular Devices).

Data were expressed in percentage of control conditions (no plant extract=100%). All values were expressed as mean+/− SEM (s.e.mean) of the 6 wells. Statistical analyses on the different conditions (ANOVA followed by Dunnett's test when allowed, using GraphPad Prism software) are made.

d) Results

The highest doses (500, 100, and 50 µg/mL) were toxic after 2 days of culture, no analysis of these conditions was done.

The results are on FIG. 2. The treatment with Plant extract WEB-2 (100, 500 ng/mL and 1 µg/mL) showed significant increase of neurite network after 3 days of treatment. The extract was able to induce a significant neurite outgrowth of cortical neurons. No effect was observed for the 2 highest doses (5 and 10 µg/mL) and for the lowest dose (50 ng/mL).

Additionally, the total number of cortical neurons were significantly increased after 3 days of treatment with WEB-2 (50, 100, 500 ng/mL, 1 µg/mL). This effect was probably due to a preventive effect of the extract against the spontaneous apoptosis observed in culture and after plating (Horisberger 2006. In Vitro Cell Dev Bio 1 Anim. May-June; 42(5-6):143-8.). Again, the 2 highest doses were not significantly active.

At day 5, the treatment with WEB-2 (all doses) showed significant increase of neurite network (See FIG. 3). Interestingly, the effect was slightly decreasing with the dose (at the highest dose, the plant extract displayed less efficacy). The extract was able to induce a significant neurite outgrowth of cortical neurons. Similarly, a large significant effect was observed on the total number of cortical neurons. A protective effect was again seen for all doses. This effect was probably due to a preventive effect of the extract against the spontaneous apoptosis observed in culture and after plating. Again, the effect seemed to be dependent of the dose.

f) Conclusion

After observation of neurons, the neurons treated with WEB-2 (all doses and especially 500 µg/mL) displayed longer and more important neurite network than the one observed with reference test compound BDNF. The WEB-2 composition seemed acting on neurite outgrowth creating and improving the neurite network EXAMPLE 12: EFFECT OF THE COMPOSITION OF THE INVENTION ON THE EXPOSITION TO GLUTAMATE This study investigated the neuroprotective effect of the composition WEB-2 on rat primary cortical cultures following exposure to glutamate (40 µM, 20 min application), an in vitro AD model.

a) Culture of Cortical Neurons

Pregnant Wistar females rat (JanvierLabs, France) at 15 days of gestation were killed by cervical dislocation. The foetuses were prepared as in example 11.

Once obtained, the cells were seeded at a density of 30,000 per well in 96-well plates precoated with poly-L-lysine (Batch: 3102256, Corning Biocoat) and were cultured at 37° C. in an air (95%)-$CO_2$ (5%) incubator. The medium was changed every 2 days. The cortical neurons were intoxicated with glutamate solution.

b) Intoxication with the Glutamate

On day 13 after culture, glutamate (Batch: 061M0030V, Sigma) was added into cell culture to a final concentration of 40 µM diluted in control medium for 20 min. After 20 min, the cells were washed-out and new fresh medium containing or not WEB-2 was added for 48 h additional time.

WEB-2 (500 ng/mL, 1, 5, 10, 50, 100 and 500 µg/mL and 1 mg/mL) were solved and diluted in culture medium and then pre-incubated with primary cortical neurons for 1 hour before the glutamate application, on were added in co-incubation, or 4, 8 and 12 h after glutamate application.

The following conditions were assessed:
Control (culture medium)
+ glutamate (40 µM, 20 min)
+ glutamate (40 µM, 20 min)+WEB-2 (at each concentration)

c) Immunostaining: Neuron Survival

After 48 hours of glutamate intoxication, cells were fixed by a cold solution of ethanol at 95% (Batch: SZBD1470V, Sigma) and acetic acid 5% (Batch: SZBD1760V, Sigma) for 5 min at −20° C. After permeabilization with 0.1% of saponin (Batch: BCBJ8417V, Sigma), cells were incubated for 2 h with mouse monoclonal antibody anti microtubule-associated-protein 2 (MAP-2) (Batch: 063M4802; Sigma) at dilution of 1/400 in PBS containing 1% foetal calf serum and 0.1% of saponin.

This antibody was revealed with Alexa Fluor 488 goat anti-mouse IgG at the dilution of 1/400 in PBS containing 1% foetal calf serum and 0.1% of saponin for 1 h at room temperature.

d) Analysis of Neurite Network

The immunolabeled cultures were automatically examined with ImageXpress equipped with a LED at ×20 magnification. For each condition (6 culture wells), 30 automatically fields per well (representing ~80% of the total surface of the well) were analyzed. The total number of neurons and neurite length were automatically analyzed using MetaXpress software.

e) Results

Glutamate (40 µM-20 min) applied on primary cortical neuron culture induced a significant neuronal death and neurite network loss.

WEB-2, tested at 100 and 500 µg/mL showed a clear and significantly neuro-protective effect both on the neuron survival and on the neurite network when added in pretreatment (1 h before the glutamate application) (FIG. 4).

Similarly at 500 µg/mL added in co-application with glutamate, WEB-2 was still able to protect neuron and neurite network from glutamate injury (FIG. 5). The most active dose of WEB-2 was 500 µg/mL. At this concentration the neurite network was fully protected from glutamate injury.

However, the composition WEB-2 was unable to rescue neurons when applied 4 h or more after the glutamate insults (FIG. 6).

EXAMPLE 13: STUDY OF THE TOXICITY OF THE PLANT EXTRACTS TOWARDS NEURITE

The aim of this study was to test 2 different extracts (WEB-1 and WE-2 at different concentrations: 500 ng/mL, 1, 5, 10, 50, 100, 500 µg/mL and 1 mg/mL) on neuritogenesis and neuron survival on primary cortical neuron culture after 3 day incubation.

a) Culture of Cortical Neurons

Pregnant Wistar females rat (JanvierLabs, France) at 15 days of gestation were killed by cervical dislocation. The foetuses were prepared as in example 11.

Once obtained, the cells were seeded at a density of 30,000 per well in 96-well plates precoated with poly-L-lysine (Batch: 3102256, Corning Biocoat) and were cultured at 37° C. in an air (95%)-$CO_2$ (5%) incubator. The medium was changed every 2 days. Cells were immediately incubated with or without WEB-1 or WE-2 (6 wells per condition).

b) Conditions of the Tests

The extracts (500 ng/mL, 1, 5, 10, 50, 100, 500 µg/mL and 1 mg/mL) were solved and diluted in culture medium and then pre-incubated with neurons immediately after cell plating.

The following conditions were assessed:
Plate 1 for day 3 evaluation
Control
+ WEB-1 (at each concentration)
Plate 2 for day 3 evaluation
Control
+ WE-2 (at each concentration)

c) Immuno Staining: Neuron Survival

On day 3 of culture, cells were fixed by a cold solution of ethanol at 95% (Batch: SZBD1470V, Sigma) and acetic acid 5% (Batch: SZBD1760V, Sigma) for 5 min at ~20° C. After permeabilization with 0.1% of saponin (Batch: BCBJ8417V, Sigma), cells were incubated for 2 h with mouse monoclonal antibody anti microtubule-associated-protein 2 (MAP-2) (Batch: 063M4802; Sigma) at dilution of 1/400 in PBS containing 1% foetal calf serum and 0.1% of saponin.

This antibody was revealed with Alexa Fluor 488 goat anti-mouse IgG at the dilution of 1/400 in PBS containing 1% foetal calf serum and 0.1% of saponin for 1 h at room temperature.

d) Analysis of Neurite Outgrowth and Neuronal Survival Evaluation

The immunolabeled cultures were automatically examined with ImageXpress equipped with a LED at ×20 magnification. For each condition (6 culture wells), 30 automatically fields per well (representing ~80% of the total surface of the well) were analyzed. Number of MAP-2 positive cells and neurites of MAP-2 positive cells were automatically analyzed using Custom module editor. (Molecular Devices). The total survival and neurite network was automatically analyzed using MetaXpress software (Molecular Devices).

Data were expressed in percentage of control conditions (no plant extract=100%). All values were expressed as mean+/− SEM (s.e.mean) of the 6 wells. Statistical analyses on the different conditions (ANOVA followed by Dunnett's test, using GraphPad Prism software) are made.

e) Results

The results are shown on FIGS. 7 and 8.

Figure 7A:
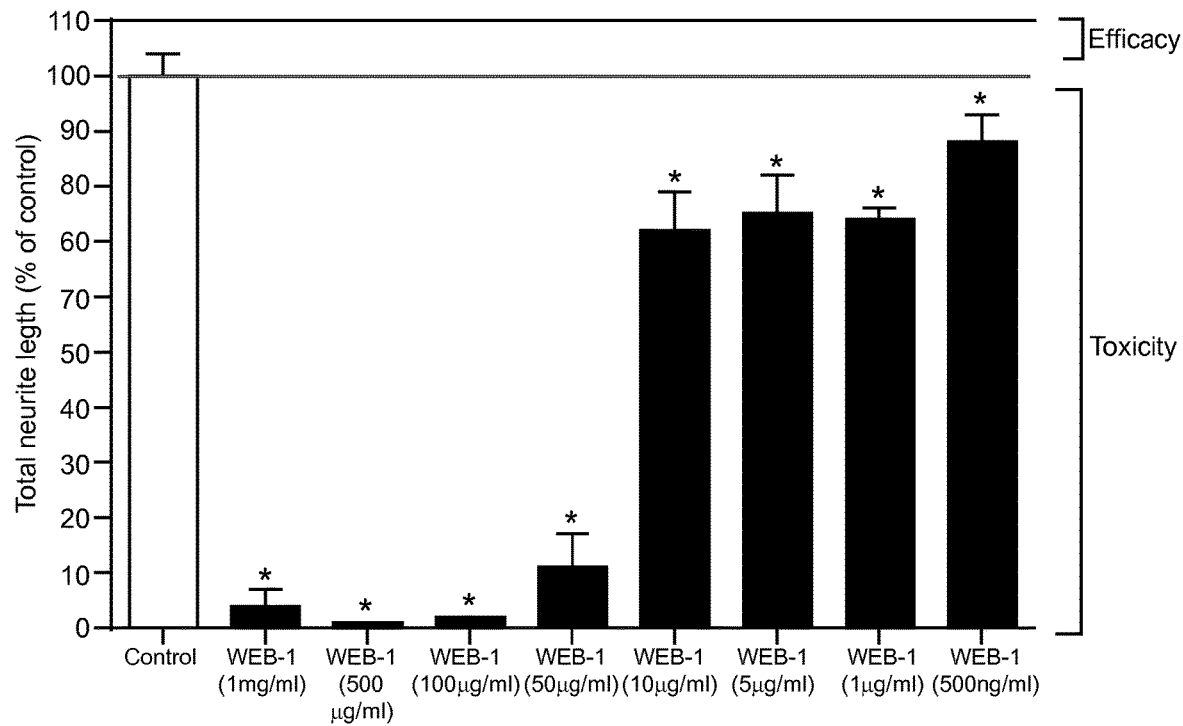
Figure 7B:
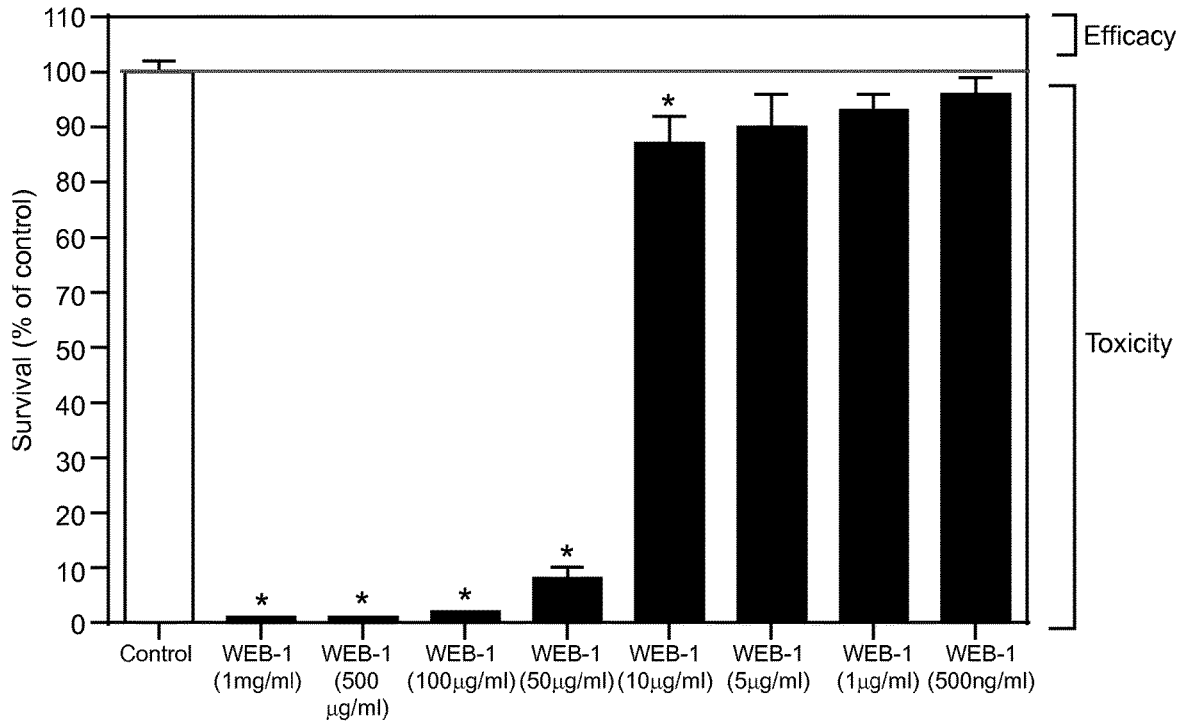

Treatment with WEB-1 did not show any effect on the neurite outgrowth (FIGS. 7a and 7b). All the tested concentrations displayed toxicity on the neurite network (especially for the highest doses). Same remarks occur for the neuron survival, at the 5 highest doses, WEB-1 induced toxicity for neurons.

The lowest doses did not show any effect on the neuron survival (FIG. 7b) and were toxic on the neurite network (FIG. 7a).

Figure 8A:
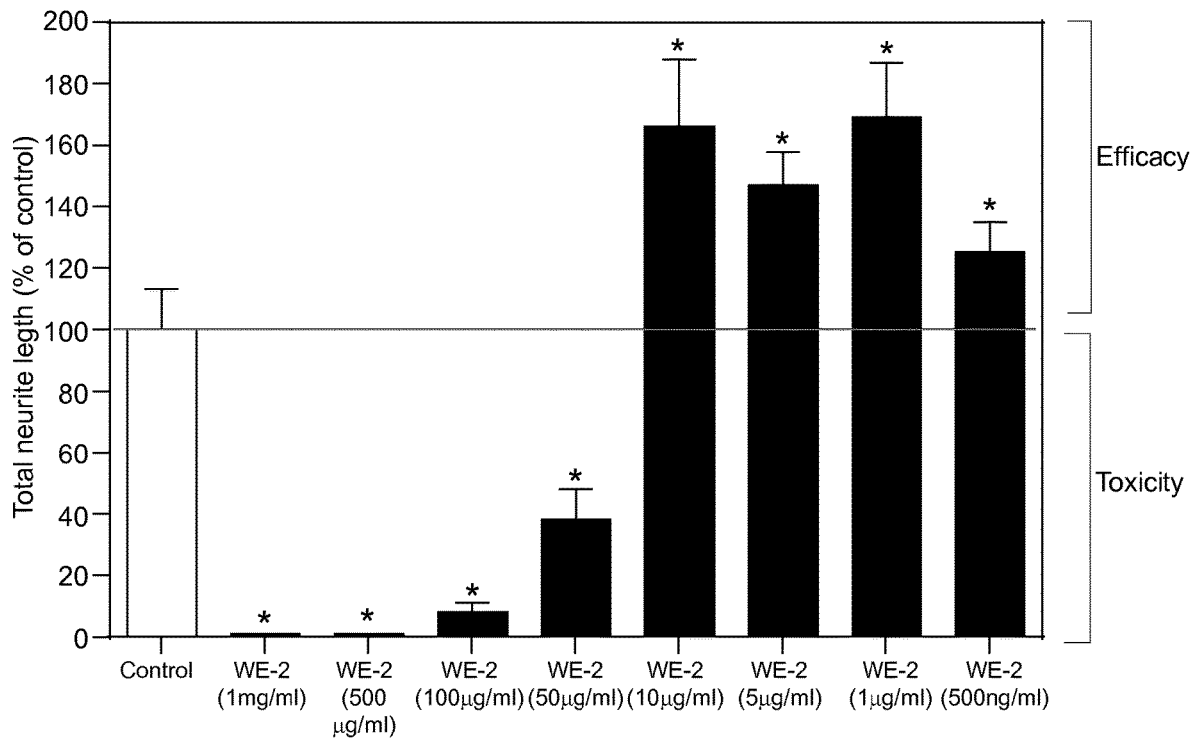
Figure 8B:
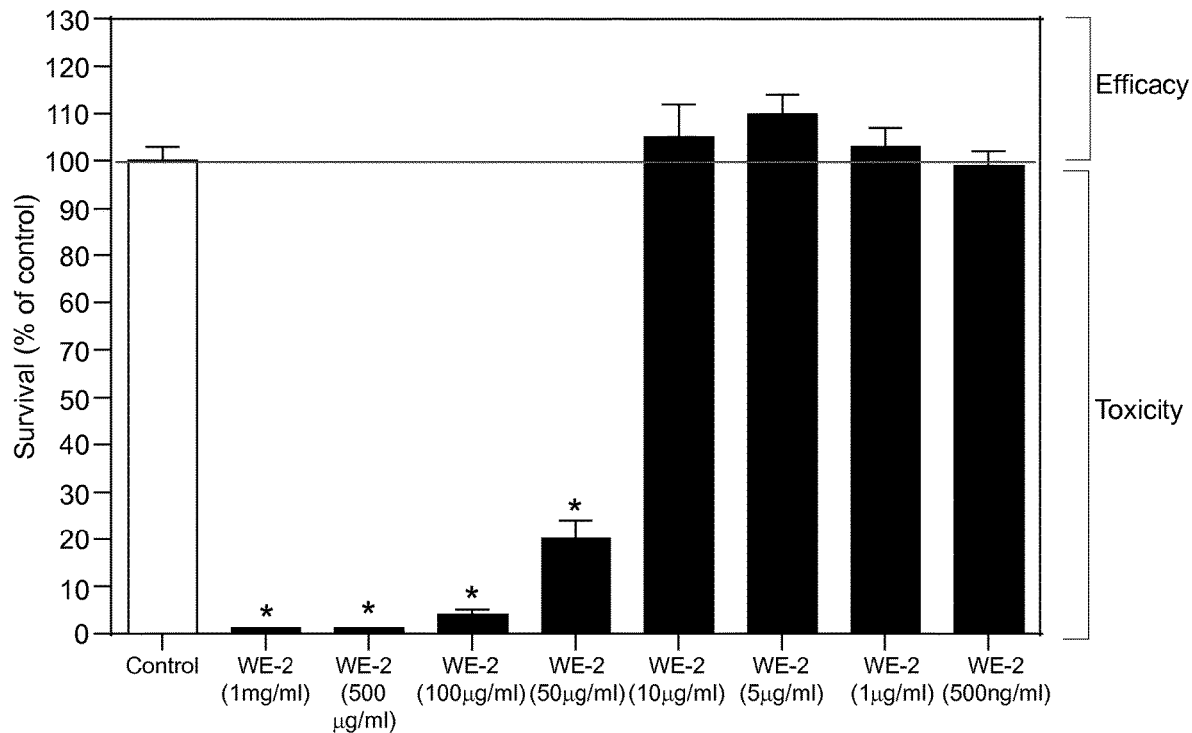

WE-2 applied on neurons for 3 days showed at the highest doses toxicity on neurite network as well as on neuron survival (FIGS. 8a and 8b). By contrast, between 500 ng/mL and 10 µg/mL concentrations, significant effect was seen on the neurite network. No effect was observed on the neuron survival.

In conclusion, WEB-1 induced large toxicity for neurite and neurons especially at the high concentrations. WE-2 was efficient inducing neurite outgrowth and promoting the neuron survival.

EXAMPLE 14: STUDY OF TWO PLANT EXTRACTS TOWARDS NEURITE

The aim of this study was to test 2 different extracts (WEB-1 and WEB-2, respectively before and after detoxifying treatment) at different concentrations: 500 ng/mL, 1, 5, 10, 50, 100, 500 µg/mL and 1 mg/mL) on neuritogenesis and neuron survival on primary cortical neuron culture after 3 day incubation.

f) Culture of Cortical Neurons

Pregnant Wistar females rat (JanvierLabs, France) at 15 days of gestation were killed by cervical dislocation. The foetuses were prepared as in example 13.

Once obtained, the cells were seeded at a density of 30,000 per well in 96-well plates precoated with poly-L-lysine (Batch: 3102256, Corning Biocoat) and were cultured at 37° C. in an air (95%)-$CO_2$ (5%) incubator. The medium was changed every 2 days. Cells were immediately incubated with or without WEB-1 or WEB-2 (6 wells per condition).

g) Conditions of the Tests

The extracts (500 ng/mL, 1, 5, 10, 50, 100, 500 µg/mL and 1 mg/mL) were solved and diluted in culture medium and then pre-incubated with neurons immediately after cell plating.

The following conditions were assessed:
Plate 1 for day 3 evaluation
Control
+ WEB-1 (at each concentration)
Plate 2 for day 3 evaluation
Control
+ WEB-2 (at each concentration) h) Immunostaining: Neuron Survival This step has been performed as in example 13.

i) Analysis of Neurite Outgrowth and Neuronal Survival Evaluation

The immunolabeled cultures have been examined as described in example 13.

j) Results

The results are shown on FIGS. 9a and 9b.

Comparison between WEB-1 i.e. a composition containing and extract of *Withania somnifera* before detoxification (according to example 1) and WEB-2 i.e. a composition containing an extract of *Withania somnifera* after the step of fermentation according to example 2 reveals that the treatment with WEB-1 did not show any effect on the neurite outgrowth and that all tested concentrations displayed toxicity on the neurite network.

On the contrary, treatment with WEB-2 composition shows an effect on the neurite outgrowth and on the neurite network, demonstrating that the composition WEB-2, treated according to the invention by combining an extraction step and a fermentation step is devoid of toxicity toward cells and is able to treat AD and other neurodegenerative disorders.

The invention claimed is:

1. A composition containing a *Withania somnifera* extract for a use to treat or prevent amyloid-related diseases in a mammal, wherein the *Withania somnifera* extract has been fermented by its incubation with a filamentous fungus in a suitable environment.

2. The composition according to claim 1, wherein the fermentation is carried out with a filamentous fungus of the family Cordycipitaceae.

3. The composition according to claim 1, further containing at least one extract from the following plants: *Emblica officinalis, Bacopa monnieri, Punica granatum, Curcuma longa, Piper longum,* or *Calendula officinalis.*

4. The composition according to claim 1, further containing an extract of *Emblica officinalis* and an extract of *Bacopa monnieri.*

5. The composition according to claim 1, comprising a quantity by weight of *Withania somnifera* of between 5 and 100 g/L of *Withania somnifera.*

6. The composition according to claim 1, comprising a quantity by weight of *Withania somnifera* at a concentration of 20 g/L, of *Emblica officinalis* at a concentration of 15 g/L and of *Bacopa monnieri* at a concentration of 15 g/L.

7. The composition according to claim 1, for a use to treat or prevent Alzheimer's disease, cerebral amyloid angiopathy, inclusion body myositis or Down's syndrome.

8. The composition according to claim 1, wherein the mammal is a human.

9. The composition according to claim 2, wherein the fermentation is carried out with a filamentous fungus of the genus *Beauveria.*

10. The composition according to claim 9, wherein the filamentous fungus is *Beauveria bassiana.*

11. The composition according to claim 5, comprising a quantity by weight of *Withania somnifera* of 20 g/L.

12. A method of treating or preventing an amyloid-related disease in a subject, comprising administering to a subject a therapeutic amount of a plant extract composition, such that said amyloid-related disease in a subject is treated or prevented, wherein said composition contains a plant extract of *Withania somnifera* according claim 1.

13. The method of claim 12, wherein said disease is Alzheimer's disease, cerebral amyloid angiopathy, inclusion body myositis, macular degeneration, or Down's syndrome.

14. The method according to claim 12, wherein amyloid fibril formation or deposition, neurodegeneration, or cellular toxicity is reduced or inhibited.

15. The method according to claim 12, wherein said subject is a human.

16. The method according to claim 12, wherein said composition causes in an Alzheimer's patient a stabilization of cognitive function, prevention of a further decline in cognitive function, or prevention, slowing, or stopping of disease progression.

17. The method according to claim 12, wherein the therapeutic composition is administered orally or intravenously.

18. The method according to claim 12, wherein said therapeutic composition is administered in a pharmaceutically acceptable vehicle.

* * * * *